(12) United States Patent
Patel (10) Patent No.: US 10,172,979 B2
(45) Date of Patent: *Jan. 8, 2019

(54) DISPOSABLE MEDICAL ITEMS MADE FROM BIOPLASTIC RESINS

(71) Applicant: Shantu Patel, Carlsbad, CA (US)

(72) Inventor: Shantu Patel, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,437

(22) Filed: Nov. 25, 2014

(65) Prior Publication Data

US 2015/0079413 A1    Mar. 19, 2015

Related U.S. Application Data (63) Continuation-in-part of application No. 14/515,468, filed on Oct. 15, 2014, now abandoned, and a continuation-in-part of application No. 14/483,155, filed on Sep. 11, 2014, now abandoned, which is a continuation-in-part of application No. 13/590,377, filed on Aug. 21, 2012, now Pat. No. 8,852,157.

(51) Int. Cl.
| | |
|---|---|
| *A61L 31/06* | (2006.01) |
| *C08L 67/04* | (2006.01) |
| *C08L 23/06* | (2006.01) |
| *B01L 3/00* | (2006.01) |
| *A61L 31/14* | (2006.01) |

(52) U.S. Cl.
CPC ............ *A61L 31/06* (2013.01); *A61L 31/148* (2013.01); *B01L 3/52* (2013.01); *C08L 23/06* (2013.01); *Y10T 428/31786* (2015.04); *Y10T 428/31938* (2015.04); *Y10T 428/31971* (2015.04)

(58) Field of Classification Search
CPC .......... A61L 31/06; A61L 31/148; B01L 3/52; Y01T 428/31971; Y01T 428/31786; Y01T 428/31938
See application file for complete search history.

(56) References Cited

U.S. PATENT DOCUMENTS

| | | | |
|---|---|---|---|
| 6,419,729 B1 * | 7/2002 | Duffy et al. ...................... 96/17 |
| 2008/0213209 A1 * | 9/2008 | Kanazawa et al. ......... 424/78.31 |
| 2009/0246250 A1 * | 10/2009 | Orgambide et al. .......... 424/423 |
| 2010/0015200 A1 * | 1/2010 | McClain et al. .............. 424/423 |
| 2010/0282623 A1 * | 11/2010 | Reshamwala ................. 206/210 |

* cited by examiner

*Primary Examiner* — Sanza L. McClendon
(74) *Attorney, Agent, or Firm* — Larry Severin (57) ABSTRACT

Disposable medical items made from bioplastic resins include a biodegradable resin selected from the group consisting of polylactic acid (PLA), cellulose based PH, polycaprolate (PCL), polybutyleneadipatetetephathalate (PBT), polyhydroxyalkanoate (PHA), green polyethylene (GPE), green polyethylene terephthalate (GPET), Poly3-hydoxybutrate-3-hydroxyhexxanate (PHBH), poly-D-lactide (PDLA), and poly-L-lactide (PLLA); a plasticizer intermixed with the resin to provide a generally homogenous bioplastic; and a device formed from the bioplastic, where the device is at least one of a vaginal speculum, a specimen container, a measuring cup, a urinal, or a medical band.

14 Claims, 12 Drawing Sheets

DISPOSABLE MEDICAL ITEMS MADE FROM BIOPLASTIC RESINS

RELATED APPLICATIONS

This application claims the benefit of the filing date of U.S. patent application Ser. No. 13/590,377, filed Aug. 21, 2012, which is incorporated herein by reference in its entirety; U.S. patent application Ser. No. 14/483,155, filed Sep. 11, 2014, which is incorporated herein by reference in its entirety; and U.S. patent application Ser. No. 14/515,468, filed Oct. 15, 2014, which is incorporated herein by reference in its entirety.

BACKGROUND OF THE INVENTION

The present invention generally relates to disposable, biodegradable items and more specifically to disposable items made from bioplastic resins.

Environment and sustainability have become increasingly important factors in the design and specification of medical items and their safe disposal after use. Due to higher social responsibility and environmental concerns, corporations are being driven to produce more sustainable and environmentally safe products through government regulations, by institutional investors, and through consumer demand.

Bioplastic resins include Polylactic acid (PLA), cellulose based PH, polybutylene adipate terephthalate (PBT) and polycaprolate (PCL), from corn and cellulose; green polyethylene, (GPE) and green polyethylene terephthalate (GPET also known as GPETE) from sugarcane; and Poly3-hydoxybutrate-3-hydroxyhexxanate (PHBH) from a fermentation process using glucose and propionic acid as the carbon source for Alcaligenes eutrophus. PHA polyhydroxyalkanoate) is derived by plant fermentation. Poly L lactide (PLLA) and poly D lactide (PDLA) are forms or homopolymers of PLA. PLA, PDLA, and PLLA are especially compostable and can be degraded to make eco-friendly compost or humus. Bioplastic resins include PLA, PHA, PCL, PH, PBT, GPE, GPET, PHBH, PDLA, and PLLA.

Bioplastic resins may have advantages over plastic and glass. Bioplastic has a smaller carbon footprint than plastic or glass, and also uses less energy to form an article like a biodegradable medical device. Bioplastics are biodegradable in an industrial composting unit. Bioplastic resins are from a plant source, and when plants are grown they absorb carbon dioxide, thus decreasing carbon dioxide in the atmosphere. These advantages, namely small carbon foot prints, absorbing carbon dioxide and using less energy, are upstream advantages and the biodegradable and compostable advantages are downstream advantages. Plastic and glass disposable items have a higher carbon footprint than items made of other materials. Plastic and glass items enter the waste stream when they are disposed of, and may need incineration a process that causes release of hydrocarbons and toxins into the atmosphere and creates fly ash that ends up in landfills.

Items made from bioplastic resin such as PLA, PHA, PH, PCL PCH are all biodegradable. Compostable items may be sterilized and then shredded and composted. PLA derived polymers namely PLLA and PDLA offer higher heat distortion properties can also be used. This will allows them to be diverted from land field. Some bio resins, such as GPE and GPET, may be made from plant sources even thought they might not be fully biodegradable or compostable.

A vaginal speculum is a diagnostic instrument for dilating the opening of the vaginal cavity in order that the interior may be more easily visible for observation.

A specimen container is commonly used to collect urine, faces, human body tissue or biopsy tissue.

A urinal is commonly used in health care facilities to safely collect, temporarily store and dispose of urine form patients.

It would be desirable to provide bioplastic or compostable devices such as vaginal speculums, specimen containers, measuring cups, urinals, and medical bands.

SUMMARY OF THE INVENTION

In one aspect of the present invention, a disposable device includes a biodegradable resin selected from the group consisting of polylactic acid (PLA), cellulose based PH, polycaprolate (PCL), polybutyleneadipatetetephathalate (PBT), polyhydroxyalkanoate (PHA), green polyethylene (GPE), green polyethylene terephthalate (GPET), Poly3-hydoxybutrate-3-hydroxyhexxanate (PHBH), poly-D-lactide (PDLA), and poly-L-lactide (PLLA); a plasticizer intermixed with the resin to provide a generally homogenous bioplastic; and a device formed from the bioplastic, where the device is at least one of a vaginal speculum, a specimen container, a measuring cup, a urinal, or a medical band.

In another aspect of the present invention, a disposable device includes a biodegradable resin that is substantially free from non-compostable material; a plasticizer intermixed with the resin to provide a generally homogenous bioplastic; a device formed from the bioplastic, where the device is at least one of a vaginal speculum, a specimen container, a measuring cup, a urinal, or a medical band; and a green indicator on the device that indicates the device is substantially compostable.

DETAILED DESCRIPTION

The preferred embodiment and other embodiments, which can be used in industry and include the best mode now known of carrying out the invention, are hereby described in detail with reference to the drawings. Further embodiments, features and advantages will become apparent from the ensuing description, or may be learned without undue experimentation. The figures are not necessarily drawn to scale, except where otherwise indicated. The following description of embodiments, even if phrased in terms of "the invention" or what the embodiment "is," is not to be taken in a limiting sense, but describes the manner and process of making and using the invention. The coverage of this patent will be described in the claims. The order in which steps are listed in the claims does not necessarily indicate that the steps must be performed in that order.

Disposable plastic articles used in medical offices, hospitals and healthcare industries may be made from sustainable, environmentally friendly bioplastic resins and may be safely disposed without further environmental impact. Embodiments of disposable articles may be made from bioplastic resin, which include PLA (PLLA and PDLA), PHA, PCH, PCL, PH, PBT, GPE, and GPET. Embodiments of disposable articles may include a plasticizer intermixed with the resin to provide a generally homogenous bioplastic. Embodiments may include a bioplastic vaginal speculum, specimen containers, caps and vials with measurements, medicine cups, and urinals.

Embodiments of disposable medical items may be made from bio resins for environmental advantages, using a bioresin such as PLA (including PLLA and PDLA), PHA, PBT, PH, PCH, PH, GPE, or GPET. A plasticizer intermixed with the resin to provide a generally homogenous bioplastic, and the device may be substantially made from the bioplastic. These polymers offer environmental advantages and can be in any combinations. For example, one part of a medical item can be made from PLA and another part can be from PCL or GPE, GPET. Embodiments of a disposable medical item include a vaginal speculum, a specimen container, a measuring cup, a urinal, or a medical bands.

An embodiment of a vaginal speculum may include a bivalve vaginal speculum having an upper blade and a lower blade, rotatably attached with a hinge. The device is in a closed configuration when the speculum is inserted to facilitate its entry and in an open configuration after insertion into its final position. An embodiment of a vaginal speculum may have a forked connector portion attached to the rear or proximal end of the upper blade, near the hinge. The forked connector provides an opening so that the area between the blades may be viewed and accessed through the opening, after the device is inserted. The forked connector has a tab at the rear that helps the user rotate the upper blade, to open and close the device. A flexible arm with ratchet teeth extends from the handle to provide a locking mechanism that locks the blades in place.

Embodiments of a whole speculum may be disposable after a single use. The lower blade may act as part of the handle and may house a portable or rechargeable light or illumination device. The illumination device may be mounted on either blade, may be stationary or portable, and may connect to as wall unit or batteries for power. Embodiments of speculums may vary in size, such as small (W ⅞×L 4 inches), medium (W 1⅛×L 4 inches), and large (W 1⅜×L 4½ Inches). Embodiments of speculums may be made from bio resins.

A human biological specimen container may have a specific size and shape. Embodiments of specimen containers may vary in size from 2 to 4 oz. and may have graduated markings in ounces or milliliters ranging from 0-2 or 0-4 oz. or 0 to 120 ml. The shape may be that of a cup or cylinder with a lid. The container may be non-sterile or sterile and individually packed in a sterile pouch. The specimen container can be empty or can have a reagent like formaldehyde. Embodiments of specimen containers may be made from bio resins.

An embodiment of a medicine cup may be particularly intended to be used for portioning medicine in a solid or liquid state, such as one to two fluid ounces. A medicine cup may made from paper or plastic such as polypropylene. The medicine cup may include a circular wall. The cup may be generally cylindrical or may conically decrease from a top open edge towards a closed bottom edge. The wall may have a top edge or rim that forms an open aperture. The wall may be straight, to form a cylinder, or may slant slightly inward towards the bottom to form a portion of a cone with a closed bottom.

A space from the open top to the closed bottom may be a distance that is at least one-half the total distance between said top edge and bottom. The cup may be marked on the lateral wall with graduated marking in millimeters, ounce or drams. The cups can vary in size from one ounce to eight ounce in size, and may have a lid. The lid shape will correspond to the conical angle of said outer top open wall of the cup. Embodiments of medicine cups may be made from bio resins.

An embodiment of a urinal may store and dispose of urine from patients. Embodiments of urinals may be manufactured by blow-molding from a suitable polymer, such as polyethylene. An embodiment of a urinal may have a body having a lower wall, an upper mouth, and front, side, and back walls. The walls may form a unitary handle projecting from the body, near the upper mouth, toward a lower portion of the front wall. The walls may define a gap between the handle and an upper portion of the front wall.

An embodiment of a urinal may have a cap, adapted to be snap-fitted around a margin of the upper mouth. The cap may be releasably attached to the handle, where the handle meets the body, via a tether that is unitary with the cap. The urinal may be marked on the lateral wall with graduated marking in millimeters or ounce. The size and shape of the urinal can vary.

Figure 1:
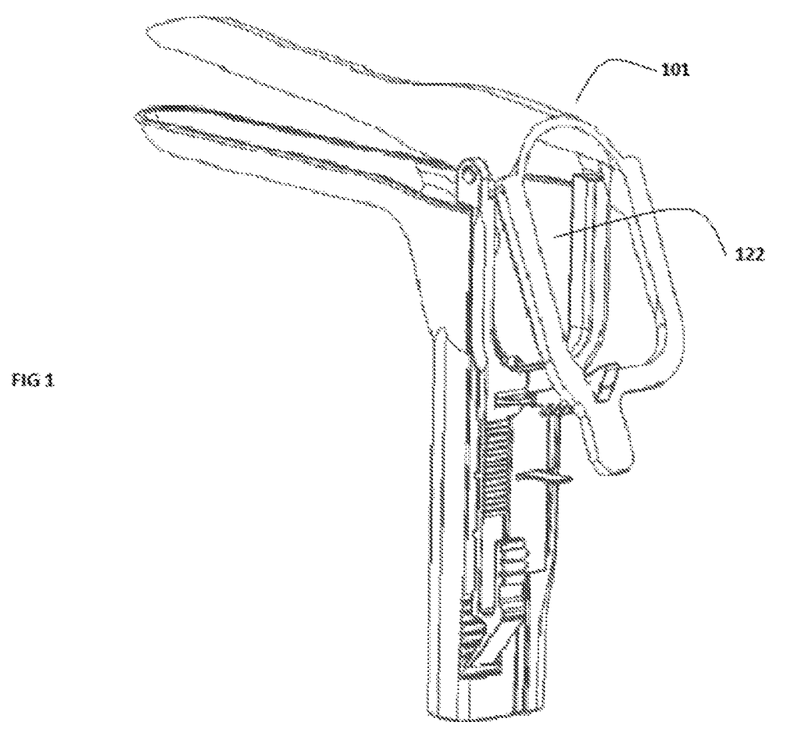
FIG. 1 depicts an embodiment of a vaginal speculum according to the present invention.

As depicted in FIG. 1, an embodiment of the present invention may include a vaginal speculum 101. The vaginal speculum 101 may be made of bioplastic materials may include three components which are assembled to make the vaginal speculum. The components may include a translucent upper blade 102, a translucent lower blade and handle portion 104, and a forked connector which may be translucent or opaque. Upper blade 102 may form a dome and lower blade 104 may form a trough. Embodiments of a vaginal speculum may bear a compostable symbol.

Figure 2:
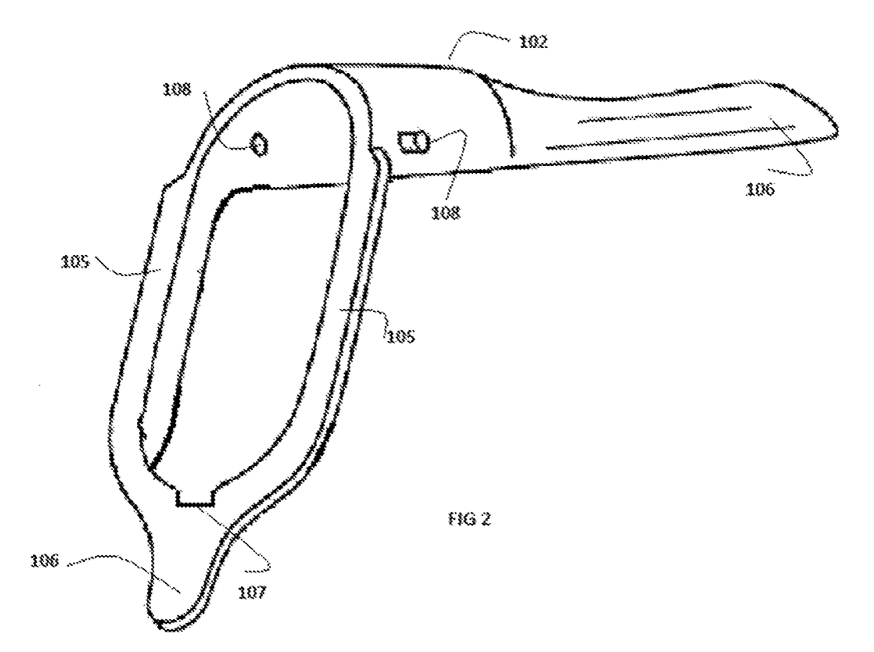
FIG. 2 depicts an upper blade of the embodiment of FIG. 1.

As depicted in FIG. 2, an embodiment of an upper blade 102 may have a dome or trough shaped distal end 106. The upper blade 102 may have a rear U shaped rim 105 with a tab 106 and a locking slot 107 above the tab 106. Upper blade 102 may have a pins 108 that attach the upper blade 102 to the lower blade.

Figure 3A:
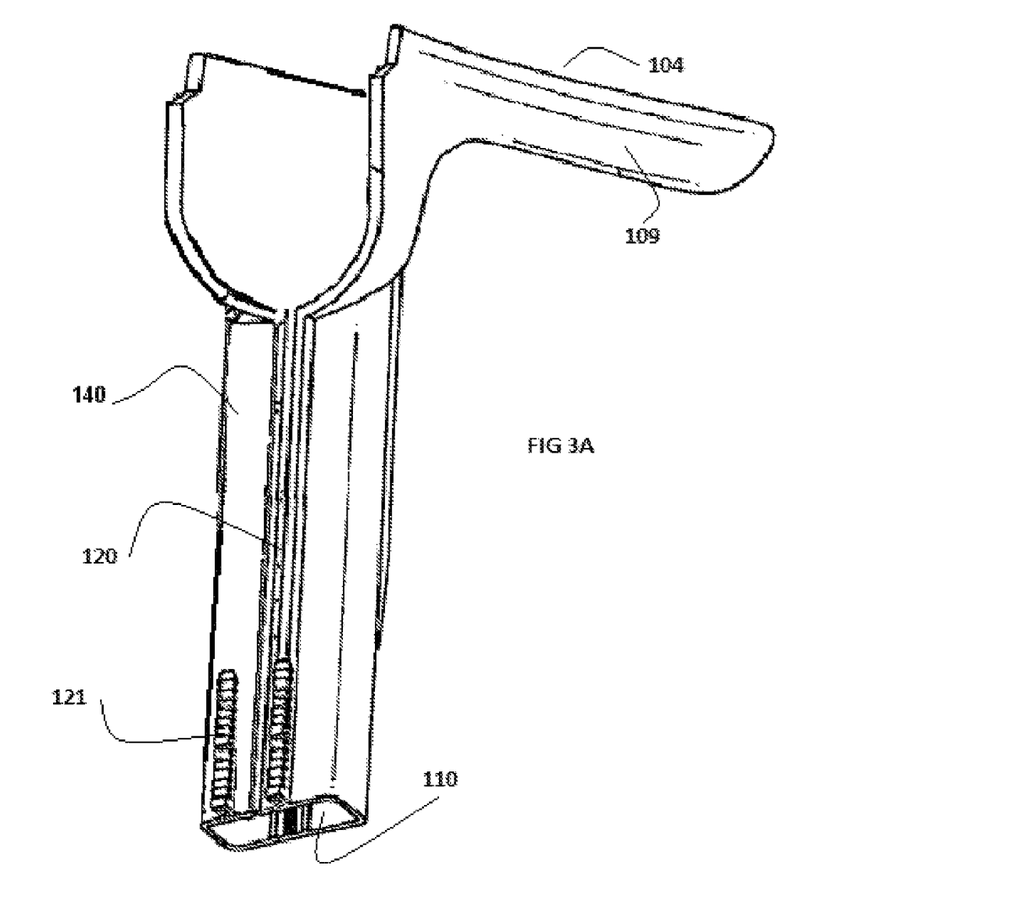
FIGS. 3A and 3B depict a lower blade of the embodiment of FIG. 1.
Figure 3B:
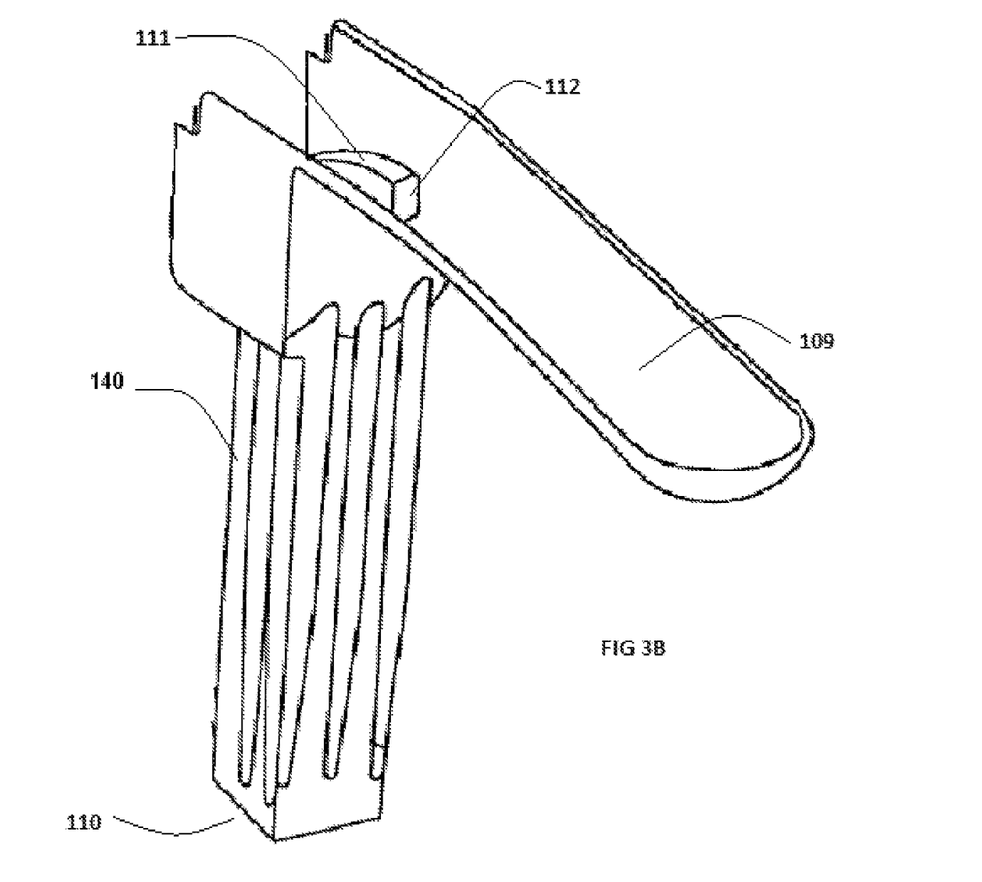

As depicted in FIGS. 3A and 3B, an embodiment of a lower blade 104 may include a handle portion 140 and a trough shaped distal end 109. The handle portion 140 may have a light housing unit 110 that receives an illumination unit, which may be portable and rechargeable or may be reusable. The light housing unit 110 may include a light pipe 111 which ends in a distal light emitting surface 112. The light housing unit may a separate illumination device or may be built into the handle portion 140.

Figure 4:
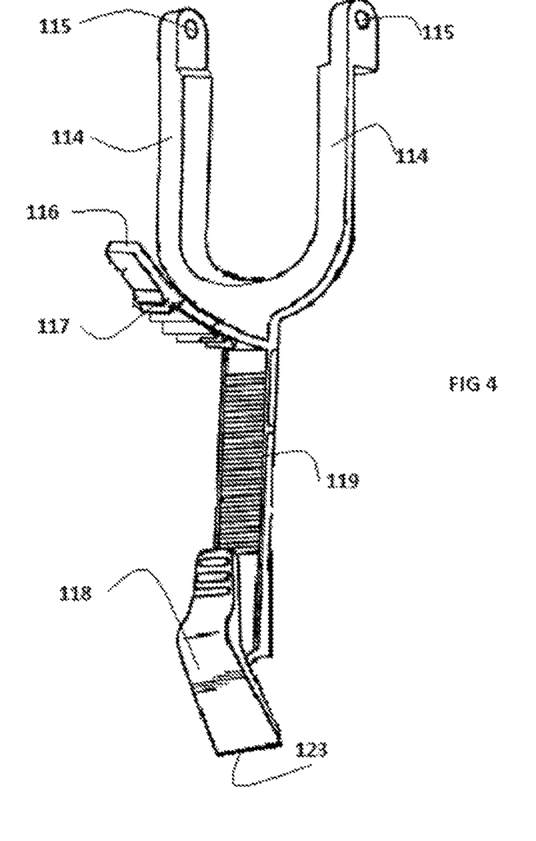
FIG. 4 depicts a forked connector of the embodiment of FIG. 1.

As depicted in FIG. 4, an embodiment of a forked connector may be opaque and may have flexible appendages. The forked connector may be made of bio resin, preferably bio resins other than PLA, namely, PHA, PCH, PCL, PH, GPE, and GPET. The forked connector may have upper U shaped arms 114 which have circular mounting holes 115 on top to receive the pins on the upper blade when assembled. The forked connector may have a flexible arm 116 with ratchet teeth 117 on a bottom surface that engage with locking slot 107. The flexible arm 116 may be upwardly curved in a convex configuration. The lower part of the forked shaped connector may have a flexible, pivotable tab 118 and a grooved surface 119 for gripping the flexible arm 116. The operator may slide the forked connector up and down along grooved slider channels 120 in the handle portion 140. The lower margin of the pivotable tab 123 may lock into external teeth 121. The up and down motion allows the operator to vary the aperture of the speculum opening 122.

Figure 5:
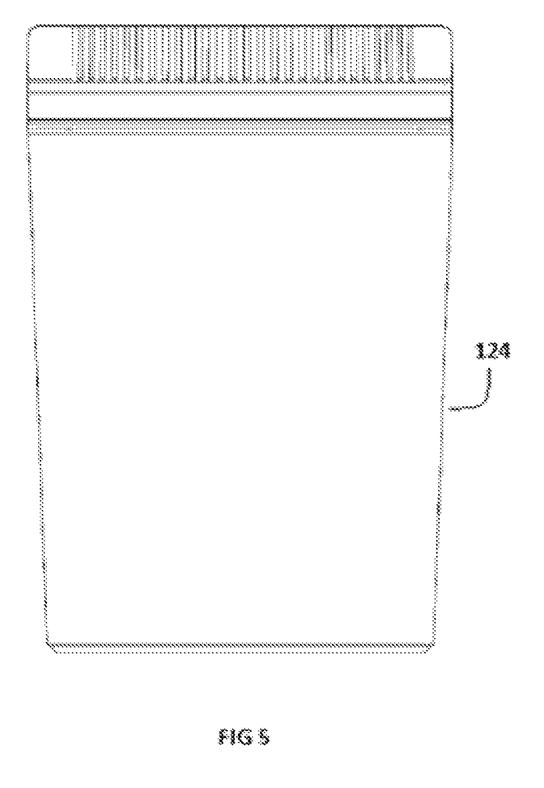
FIG. 5 depicts an embodiment of a specimen container according to the present invention.

As depicted in FIG. 5, an embodiment of a specimen container 124 for human biological specimen collection may include a cap and vial made substantially or entirely of injection molded bio resins, namely PLA (including PLLA and PDLA), PHA, PH, PCH, PCL, GPE, and GPET. The cap and vial may be colored green and may bear a compostable symbol.

Figure 6:
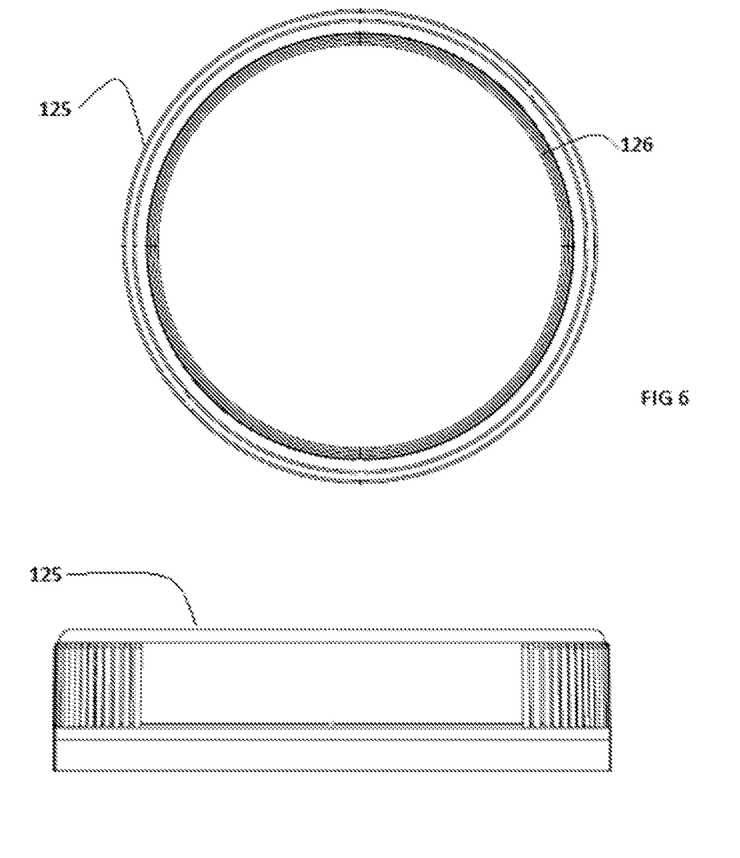
FIG. 6 depicts a cap of the embodiment of FIG. 5.

As depicted in FIG. 6, an embodiment of a cap 125 for specimen container may have a flexible annular member 126 around the underside rim of the cap. The annular member 126 engages with the top of the vial to form a water and air tight. The seal comes into play when the cap 125 and vial are assembled by closing the cap tightly, which may be held together by screw threads.

Figure 7A:
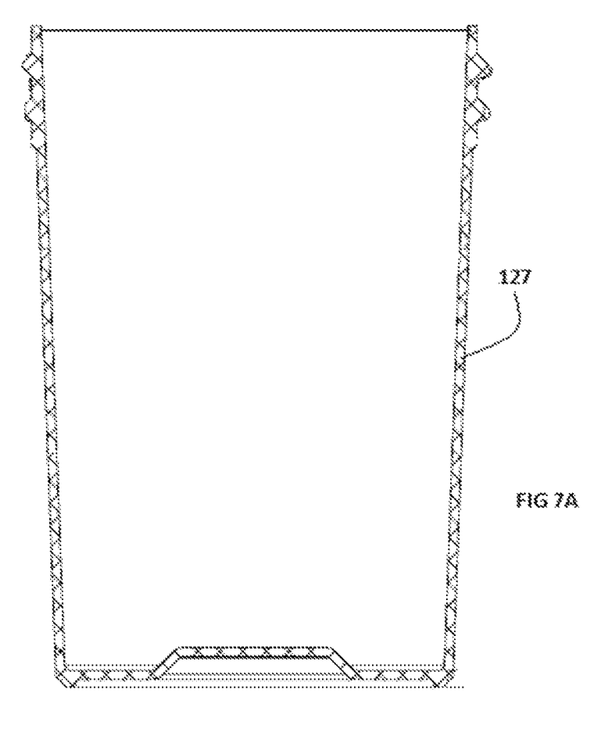
FIGS. 7A and 7B depict a vial of the embodiment of FIG. 5.
Figure 7B:
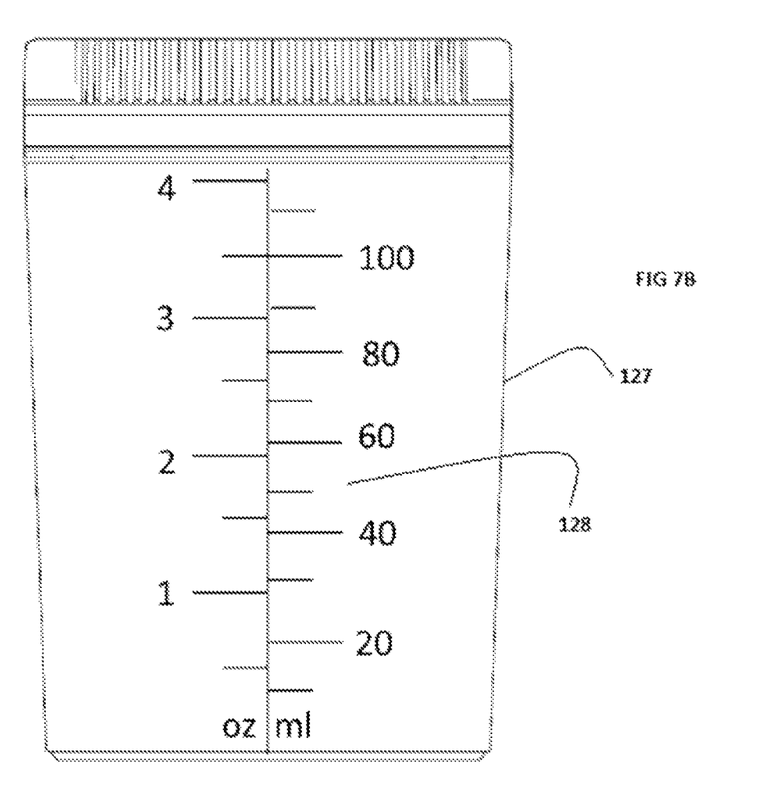

As depicted in FIGS. 7A and 7B, a vial 127 may have a capacity of 2 to 4 oz. in size and may have graduated measurements 128 for volume marked on the side of the vial 127. Embodiments of graduated measurements 128 may indicate volume levels from 0 to 4 oz. or 0 to 120 ml. or both so that a user may see the level and thereby determine the volume of specimen in the container.

Figure 8:
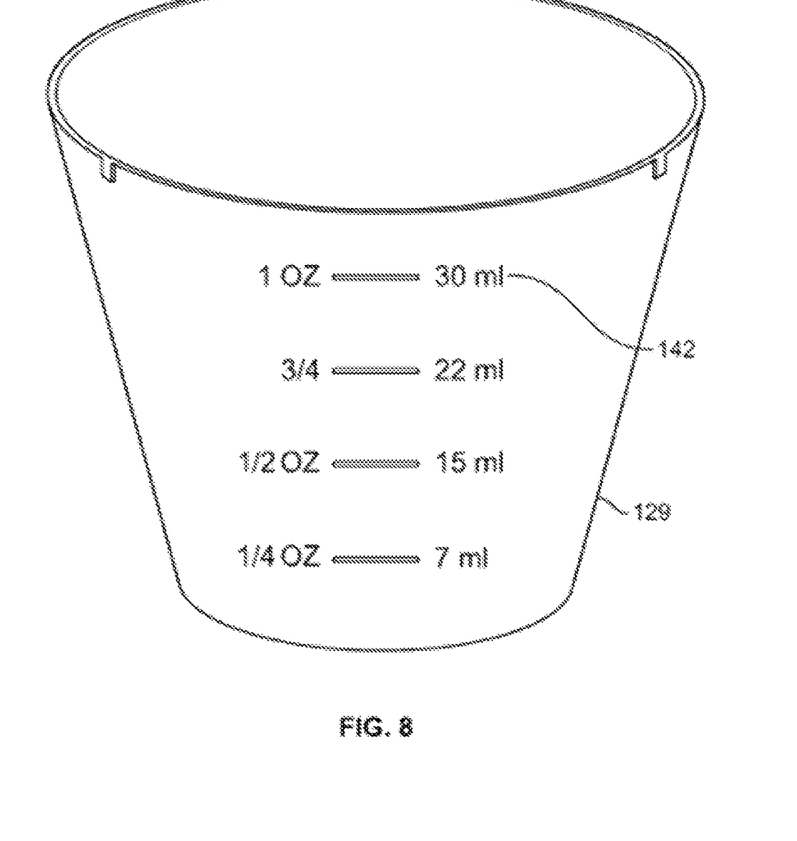
FIG. 8 depicts an embodiment of a measuring cup according to the present invention.

As depicted in FIG. 8, an embodiment of a medicine cup 129 or other measuring cup may be injection molded using bio plastic resins. Embodiments may include a cup shaped, truncated cone, having a flat bottom that widens to an open top. The cup 129 may be marked with graduated measurements 142 that indicate the volume of material in the cup based upon the level. Since the sides of the cup are slanted outwards, graduates measurements 142 with consistent volume spacing will tend to be closer together near the top of the cup. Graduated measurements 142 may include horizontal lines drawn or etched onto the cup 129 with appropriate labels. Graduated measurements 142 may indicate where the volume would be 1, ¾, ½, and ¼ oz., or 30, 22, 15, and 7 ml., or both.

Figure 9:
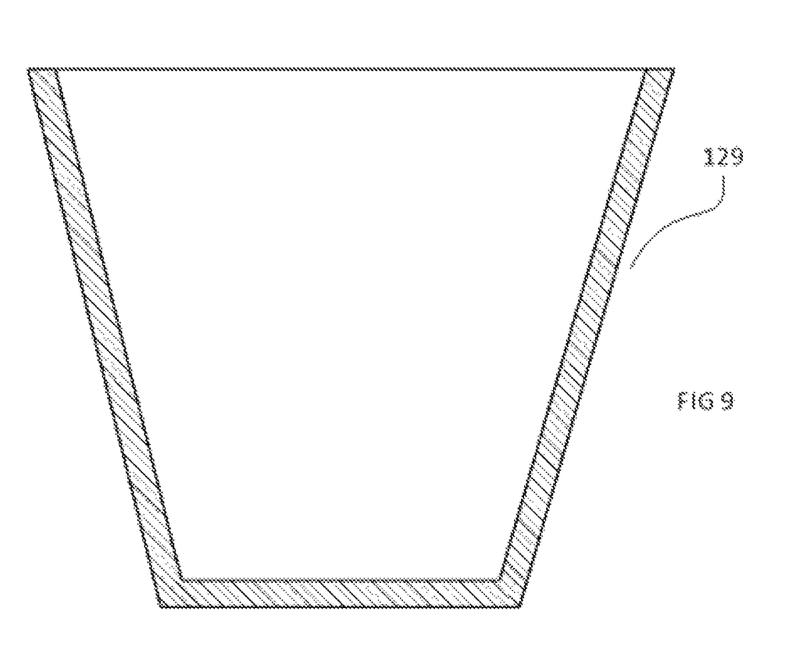
FIG. 9 depicts the cup of FIG. 8.

As depicted in FIG. 9, an embodiment of a medicine cup 129 may have walls made of a bioplastic resin mixed with a plasticizer.

Figure 10:
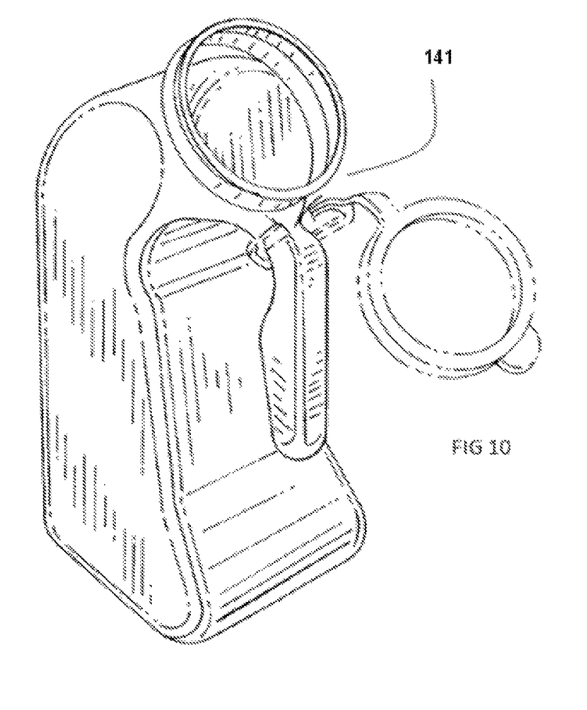
FIG. 10 depicts a urinal according to the present invention.

As depicted in FIG. 10, an embodiment of a urinal 141 may be blow molded using bioplastic resin. A urinal 130 may include a urine collection bottle with a canted opening near the top and a handle. Embodiments may include a cap which may have an elongated tab that flexibly attaches to the bottle.

Figure 11:
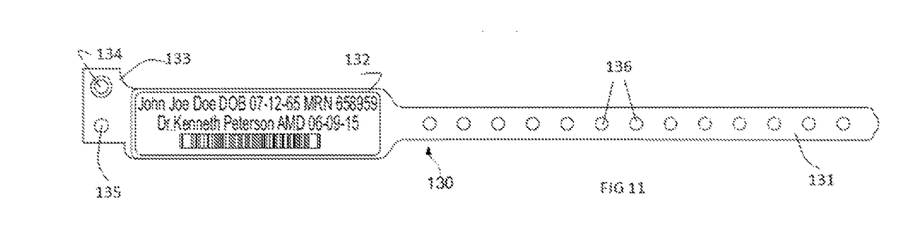
FIG. 11 depicts a medical band according to the present invention.

As depicted in FIG. 11, an embodiment of a medical band 130 may include a disposable, adjustable bracelet for a user's wrist or ankle. The medical band 130 may have an adjustable portion 131 that wraps around and attaches to the band 130, and a label portion 132 that includes patient information such as text or a barcode. A tab 133 at one end may include a reinforced aperture or lanyard 134. The tab 133 may also have a peg 135 that adjustably attaches to a one of series of holes 136 in the adjustable portion 131, to adjust the size of the band 130.

I claim:

1. A disposable device comprising:
    a device formed from a bioplastic, wherein said bioplastic is obtained by intermixing a biodegradable resin selected from the group consisting of a copolymer of a glocoloide and e-caprolactone (PCL), polybutyleneadipatetetephathalate (PBT), polyhydroxyalkanoate (PHA), green polyethylene (GPE), green polyethylene terephthalate (GPET), poly-D-lactide (PDLA), and poly-L-lactide (PLLA)
    with a plasticizer to provide a homogenous bioplastic; and
    the device formed from the bioplastic is at least one of a vaginal speculum, a specimen container, a measuring cup, a urinal, or a medical band.

2. The device of claim 1, wherein the biodegradable resin is PCL.

3. The device of claim 1, wherein the biodegradable resin is PBT.

4. The device of claim 1, wherein the biodegradable resin is PHA.

5. The device of claim 1, wherein the biodegradable resin is GPE.

6. The device of claim 1, wherein the biodegradable resin is GPET.

7. The device of claim 1, wherein the biodegradable resin is PHA and includes a poly3-hydoxybutrate-3-hydroxyhexxanate (PHBH).

8. The device of claim 1, wherein the biodegradable resin is PDLA.

9. The device of claim 1, wherein the biodegradable resin is PLLA.

10. The device of claim 1, wherein the device is a vaginal speculum.

11. The device of claim 1, wherein the device is a specimen container.

12. The device of claim 1, wherein the device is a measuring cup.

13. The device of claim 1, wherein the device is a urinal.

14. The device of claim 1, wherein the device is a medical band.

* * * * *